(12) United States Patent
Davis et al.

(10) Patent No.: US 7,717,363 B2
(45) Date of Patent: May 18, 2010

(54) DEGRADABLE POLYMERS AND METHODS OF PREPARATION THEREOF

(75) Inventors: Mark E. Davis, Pasadena, CA (US); Kenneth W. Wright, Rolling Hills Estate, CA (US); Ryan K. Zeidan, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 11 days.

(21) Appl. No.: 12/151,659

(22) Filed: May 8, 2008

(65) Prior Publication Data

US 2008/0249281 A1 Oct. 9, 2008

Related U.S. Application Data

(62) Division of application No. 11/316,387, filed on Dec. 21, 2005, now abandoned.

(60) Provisional application No. 60/638,511, filed on Dec. 22, 2004.

(51) Int. Cl.
| | |
|---|---|
| B02C 19/00 | (2006.01) |
| C08G 75/00 | (2006.01) |
| C08G 75/14 | (2006.01) |
| C08G 79/08 | (2006.01) |
| C08G 79/02 | (2006.01) |

(52) U.S. Cl. ............................ 241/1; 528/373; 528/387; 528/394; 528/398

(58) Field of Classification Search ................ 528/373, 528/394, 398; 241/1
See application file for complete search history.

(56) References Cited

U.S. PATENT DOCUMENTS

| | | | | |
|---|---|---|---|---|
| 2,676,165 | A |  | 4/1954 | Fettes |
| 3,943,107 | A | * | 3/1976 | Seltzer et al. ................ 525/419 |
| 4,105,646 | A | * | 8/1978 | Winter ........................ 525/422 |
| 4,376,193 | A | * | 3/1983 | Bertozzi ....................... 528/59 |
| 4,740,438 | A | * | 4/1988 | Krishnamurthy ............. 430/17 |
| 5,153,305 | A | * | 10/1992 | Tsuchida et al. ............. 528/373 |
| 5,342,724 | A | * | 8/1994 | Wilson ........................ 430/114 |
| 5,399,658 | A | * | 3/1995 | Archey et al. ................ 528/198 |
| 5,418,127 | A | * | 5/1995 | Budz et al. ................... 430/611 |
| 5,698,564 | A | * | 12/1997 | Katsuyama et al. .......... 514/275 |
| 6,805,876 | B2 | * | 10/2004 | Leong et al. ................. 424/426 |
| 6,828,412 | B1 | * | 12/2004 | Brocchini et al. ............ 528/310 |
| 2001/0044417 | A1 | * | 11/2001 | Wolff et al. .................. 514/44 |
| 2002/0099167 | A1 | * | 7/2002 | Okubo et al. ................ 528/374 |
| 2002/0188342 | A1 |  | 12/2002 | Rykhus et al. |
| 2002/0193634 | A1 | * | 12/2002 | Feng et al. ................... 564/49 |
| 2003/0039689 | A1 |  | 2/2003 | Chen et al. |
| 2003/0124368 | A1 |  | 7/2003 | Lynn et al. |
| 2003/0175324 | A1 |  | 9/2003 | Robinson et al. |
| 2003/0232952 | A1 | * | 12/2003 | Rosen ......................... 528/44 |
| 2004/0097697 | A1 | * | 5/2004 | Senga et al. ................. 528/373 |
| 2004/0161468 | A1 | * | 8/2004 | Toumi et al. ................ 424/489 |
| 2004/0166077 | A1 | * | 8/2004 | Toumi et al. ............. 424/70.11 |
| 2004/0197716 | A1 | * | 10/2004 | Magee et al. ................ 430/488 |
| 2005/0020518 | A9 | * | 1/2005 | Wolff et al. .................. 514/44 |
| 2005/0214339 | A1 | * | 9/2005 | Tang et al. ................... 424/423 |
| 2006/0239961 | A1 | * | 10/2006 | Bentley et al. ............ 424/78.32 |
| 2008/0070786 | A1 | * | 3/2008 | Bowman et al. ............ 504/359 |

OTHER PUBLICATIONS

Fisher et al., Annu. Rev. Mater. Res., 2001, 31, p. 171-181.*
Baeyens et al., "Clinical Evaluation of Bioadhesive Ophthalmic Drug Inserts (BODI) for the Treatment of External Ocular Infections in Dogs," *J. of Controlled Release* 85:163-163 (2002).
Baeyens et al., "Optimized Release of Dexamethasone and Gentamicin from a Soluble Ocular Insert for the Treatment of External Ophthalmic Infections," *J. of Controlled Release* 52:215-220 1998.
T. A. Barbolt Chemistry and Safety of Triclosan, and Its Use as an Antimicrobial Coating on Coated VICRYL Plus Antibacterial Suture (Coated Polyglactin 910 Suture with Triclosan) *Surgical Infections* vol. 3, Suppl. 1:S-45-S-53 (2002).
Boccaccini et al., "Composite Surgical Sutures with Bioactive Glass Coating," *J. Biomed Mater Res.* Part B, Appl. Biomater 67B:618-626 (2003).
Castro et al., "Ciprofoxacin Implants for Bone Infection. In Vitro-In Vivo Characterization," *J. Control Release* 93:341-354 (2003).
Chang et al., "Two Clinical Trials of an Intraocular Steroid Delivery System for Cataract Surgery," *Tr. Am. Ophth. Soc.* 97:261-274 (1999).
Chang et al., "A Selective, Cell-Permeable Optical Probe for Hydrogen Peroxide in Living Cells," J. Am. Chem. Soc. 126:15392-15393 (2004).
Congdon et al., "Prevalence of Cataract and Pseudophakia/Aphakia Among Adults in the United States," *The Eye Diseases Prevalence Research Group* 122:487-494 (2004).
Deshpande et al., "Bioerodible Polymers for Ocular Drug Delivery," *Crit. Rev. in Ther. Drug Carrier Syst.* 15:381-420 (1998).
Di Colo et al., Relevance of Plymer Molecular Weight to the In Vitro/In Vivo Performances of Ocular Inserts Based on Poly(ethyleneoxide) *Int. J. of Pharma.* 220:169-177 (2001).
Di Colo et al., A Study of Release Mechanisms of Different Ophthalmic Drugs from Erodible Ocular Inserts Based on Poly(ethylene Oxide) *Eur. J. of Pharm. and Biopharm.* 54:193-199 (2002).
Donnenfeld et al., *JAMA* 290:2938 (2003).
Emerich et al., "Biocompatibility of Poly(DL-Lactide-Co- Glycolide) Microspheres Implanted Into the Brain," *Cell Transplantation* 8:47-58 (1999).
Friedberg et al., "Device Drug Delivery to the Eye," *Ophthalmology* 98:725-732 (1991).
Friedrich et al., "Pharmacokinetic Differences Between Ocular Inserts and Eyedrops," *J. of Ocular Pharm.* 12:5-18 (1996).
Holmes et al., "Birth Prevalence of Visually Significant Infantile Cataract in a Defined U.S. Population," *Ophthalmic Epidemiol.* 10:67-74 (2003).

(Continued)

*Primary Examiner*—Mark Eashoo
*Assistant Examiner*—Liam J Heincer
(74) *Attorney, Agent, or Firm*—Ropes & Gray LLP

(57) ABSTRACT

The present invention provides polymers which substantially degrade in the presence of one or more triggers, preferably light energy or hydrogen peroxide, but does not substantially degrade in the absence of one or more triggers.

9 Claims, 8 Drawing Sheets

OTHER PUBLICATIONS

Hornof et al., "Mucoadhesive Ocular Insert Based on Thiolated Poly(Acrylic Acid): Development and In Vivo Evaluation in Humans," *J. of Controlled Release* 89:419-428 (2003).

R.A. Jain, The Manufacturing Techniques of Various Drug Loaded Biodegradable Poly(Lactide-co-Glycolide) (PLGA) Devices *Biomaterials* 21:2475-2490 (2000).

Kato et la., "Feasibility of Drug Delivery to the Posterior Pole of the Rabbit Eye with an Episcleral Implant," *Inv. Ophthalmol. Vis. Sci.* 45:238-244 (2004).

H. G. Kuivila, "Electrophilic Displacement Reactions. III. Kinetics of the Reaction Between Hydrogen Peroxide and Bezeneboronic Acid," *J. Am. chem. Soc.* 76:870-874 (1954).

Kuivila et al., "Electrophilic Displacement Reactions. IX. Effects of Substituents on Rates of Reactions Between Hydrogen Peroxide and Bezeneboronic Acid," *J. Am. Chem. Soc.* 79:5659-5662 (1957).

Kunou et al., "Biodegradable Scleral Implant for Controlled Intraocular Delivery of Betamethasone Phosphate," *J. Biomed. Mater Res.* 51:635-641 (2000).

Letsinger et al. "Organoboron Compounds. X. Popcorn Polymers and Highly Cross-Linked Vinyl Polymers Containing Boron," *J. Am. Chem. Soc.* 81:3009-3012 (1959).

Loftsson et al., "The Effects of Water-Soluble Polymers on Cyclodextrins and Cycoldextrin Solubilization of Drugs," *J. Drug Del. Sct. Tech.* 14:35-43 (2004).

D. A. Loy, "Research Summary," pp. 1-6 (2005).

Mack et al., "Thermal and Photochemistry of a Pyrene Dihydrodioxin (PDHD) and Its Radical Cation: A Photoactivated Masking Group for Ortho-Quinones," *J. Am. Chem. Soc.* 126:15324-15325 (2004).

McElhanon et al., "Removable Foams Based on an Epoxy Resin Incorporating Reversible Diels-Alder Adducts," *J. of Appl. Polym. Sci..* 85:1496-1502 (2002).

Milanesi et al., "Synthesis and Photochemistry of a New Class of Photocleavable Protein Cross-Linking Reagents," *Chem. Eur. J.* 10:1705-1710 (2004).

Nelson et al., "Technique Paper for Wet-Spinning Poly(L-Lactic Acid) and Poly(DL-Lactide-Do-Glycolide) Monofilament Fibers," *Tissue Eng.* 9:1323-1330 (2003).

R. J. Olson, "Reducing the Risk of Postoperative Endophthalmitis," *Survey of Ophthalmology* 49:S55-S61 (2004).

Sasaki et al., "One-Side-Coated Insert as a Unique Ophthalmic Drug Delivery System," *J. of Controlled Release* 92:241-247 (2003).

Sauer et al., "Topical Antibiotic Before Cataract Surgery," *JAMA* 290:2937-2938 (2003).

Wadood et al., "Safety and Efficacy of a Dexamethasone Anterior Segment Drug Delivery System in Patients after Phacoemulsification," *J. Cataract Refract Surg.* 30:761-768 (2004).

Yue et al., "A Novel Polymeric Chlorhexidine Delivery Device for the Treatment of Periodontal Disease," *Biomaterials* 25:3743-3750 (2004).

Database WPI Section Ch Week 200516, Derwent Publications Ltd., London, GB, AN 2005-143308, XP002392466 & CN 1 539 385 (Univ Qinghua) Oct. 27, 2004 Abstract.

Search Report from corresponding International Application No. PCT/US2005/046697.

* cited by examiner

DEGRADABLE POLYMERS AND METHODS OF PREPARATION THEREOF

RELATED APPLICATIONS

This application is a divisional of U.S. patent application Ser. No. 11/316,387, filed Dec. 21, 2005, which claims the benefit of U.S. Provisional Patent Application 60/638,511, filed Dec. 22, 2004, the specifications of which are incorporated by reference herein.

BACKGROUND OF THE INVENTION

Implantable surgical devices such as surgical fasteners, clips, staples, partitions, stents, and sutures are typically employed in surgical procedures to hold body tissue together, to separate body tissue, and/or to promote the healing and joining of the tissue. Such surgical devices are often made from synthetic non-biodegradable and biodegradable or bioerodible polymers. Synthetic absorbable multifilament sutures such as Dexon, Vicryl, and Polysorb, commercially available from Davis & Geck (Danbury, Conn.), Ethicon, Inc. (Somerville, N.J.), and United States Surgical Corporation (Norwalk, Conn.), respectively, are well known in the industry. An advantage of non-biodegradable implants is that they generally retain their structural integrity and properties while remaining within the body. An advantage of biodegradable devices is that, once implanted, they often do not need to be removed by a separate surgical operation since they may be degraded and absorbed by the body. For example, U.S. Pat. No. 5,889,075 describes a surgical suture fabricated from a copolymer containing dioxanone, trimethylene carbonate and glycolide that is treated with gamma radiation to enhance bioabsorbability without adversely effecting handling properties.

However, non-biodegradable polymeric implants are often temporary and require removal from the body, which can traumatize the patient. While biodegradable polymers are often employed when temporary implants are needed, these devices often degrade too quickly, so that polymer structure and function is prematurely lost, or too slowly, so that prolonged polymer/implant presence interferes with normal body function. Hence, a polymer whose structure and/or function can be degraded at a selected time would be useful in surgical implants.

SUMMARY OF THE INVENTION

The compositions, systems, and methods described herein generally relate to a biocompatible polymer, wherein the polymer substantially degrades in the presence of one or more triggers, preferably light energy or hydrogen peroxide, but does not substantially degrade in the absence of one or more triggers. For example, in preferred embodiments, the polymer does not substantially degrade under physiological conditions in the absence of one or more triggers.

In certain embodiments, the polymer substantially degrades through the cleavage of carbon-carbon bonds, carbon-oxygen bonds, carbon-nitrogen bonds, carbon-boron bonds, nitrogen-nitrogen bonds, sulfur-sulfur bonds, boron-oxygen bonds, oxygen-phosphorous bonds, or a combination thereof. In preferred embodiments, the polymer substantially degrades through the cleavage of carbon-carbon bonds, carbon-oxygen bonds, carbon-boron bonds, sulfur-sulfur bonds, boron-oxygen bonds, or a combination thereof.

In some embodiments, the polymer substantially degrades through the cleavage of carbon-carbon bonds, carbon-oxygen bonds, or sulfur-sulfur bonds, and at least one trigger is light energy.

In other embodiments, the polymer substantially degrades through the cleavage of carbon-boron bonds and optionally boron-oxygen bonds, and at least one trigger is hydrogen peroxide.

In some embodiments, the polymer comprises carbon-boron bonds and optionally boron-oxygen bonds in the backbone of the polymer. For example, the carbon-boron bonds in the backbone may be $sp^2$ carbon-boron bonds, such as arylboron bonds.

In certain embodiments, the boron atoms of the carbon-boron bonds in the backbone of the polymer have the substitution:

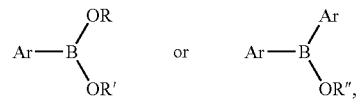

wherein
Ar is an aryl or heteroaryl moiety that is part of the polymer backbone;
R is an alkyl moiety that is part of the polymer backbone;
R' is H, lower alkyl, or an alkyl moiety that is part of the polymer backbone; and
R" is H or lower alkyl, wherein optionally R and R' together with any intervening atoms form a 5- to 7-membered ring.

In certain embodiments, the polymer substantially degrades through one or more electrocyclic or retro-cycloaddition reactions. In other embodiments, the polymer substantially degrades through homolytic cleavage of one or more chemical bonds. In further embodiments, the polymer substantially degrades through oxidation of atoms in the polymer.

In some embodiments, the polymer substantially degrades in the presence of both a first and second trigger; but the polymer does not substantially degrade in the presence of either the first or second trigger alone.

In certain embodiments, the first or second trigger is light energy, for example, light energy of a suitable wavelength to induce homolytic cleavage of one or more chemical bonds of the polymer. In other embodiments, the first or second trigger is hydrogen peroxide. For example, in preferred embodiments, light energy is the first trigger and hydrogen peroxide is the second trigger.

In certain embodiments, the polymer substantially degrades through the cleavage of sulfur-sulfur bonds and the first trigger is light energy and the second trigger is hydrogen peroxide, for example, light energy having a wavelength in the ultraviolet region, for example a wavelength of between about 200 and 300 nm, such as between about 250 and 270 nm. In such instances, it is preferable that the polymer comprises sulfur-sulfur bonds in the backbone of the polymer. For example, the polymer may comprise substituted or unsubstituted bis(aminoaryl)-disulfide monomers, such as substituted or unsubstituted bis(4-aminophenyl)-disulfide monomers.

In some embodiments, the polymer further comprises substituted or unsubstituted monomers that do not contain bonds which undergo cleavage the presence of one or more triggers. For example, in certain embodiments, the polymer further comprises substituted or unsubstituted adipic acid, terephthalic acid, or PEG diacid monomers.

In some embodiments, the polymer has a structure represented according to Formula III:

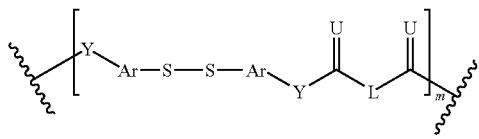

(III)

wherein,

Ar, independently for each occurrence, is an aryl or heteroaryl group, such as a substituted or unsubstituted phenyl group;

U is O or S, preferably O;

Y is NR", S, or O, particularly NR", such as NH;

L is a linking group;

R" is H or lower alkyl; and m is an integer greater than 10.

The present invention also contemplates a method for the degradation of a polymer in a patient, comprising:

a) subjecting the polymer to an amount of a first trigger; and b) subjecting the polymer to an amount of a second trigger in the presence of the first trigger;

thereby degrading the polymer in the patient, wherein the polymer substantially degrades in the presence of both the first and second trigger, and the polymer does not substantially degrade in the presence of either the first or second trigger alone.

The present invention also contemplates a biocompatible implant comprising one or more polymers and/or composition(s) of polymers as described herein. In some embodiments, the implant is a suture and/or a clip, for example for holding tissue in place in a patient. In other embodiments, the implant is a partition for separating tissues in the body of a patient. In certain embodiments, the implant is a stent.

The present invention also contemplates coatings comprising one or more polymer and/or composition(s) of polymers as described herein. In some embodiments, the coating is an adhesive, such as an adhesive suitable for oral applications. In certain embodiments, the coating is an adhesive suitable for oral applications such as dental applications, for example, dental applications that comprise permanent or temporary fixation of a natural or synthetic tooth or tooth component. In some embodiments, the oral applications comprise orthodontic applications, such as temporary fixation of a device or structure to a tooth, such as one or more spacers and/or braces.

In certain embodiments, the coating is a barrier, for example, to separate environments on either side of the coating.

The present invention also contemplates compositions comprising one or more polymers and/or composition(s) of polymers as described herein in combination with one or more therapeutic agents.

The present invention also contemplates methods for the preparation polymers and composition of polymers as described herein. In some embodiments, the invention comprises a method for the preparation of a polymer according to Formula III:

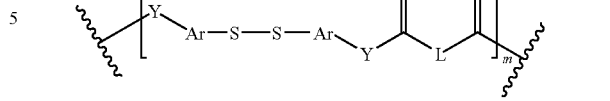

(III)

comprising reacting a monomer of Formula A with a monomer of Formula B or a monomer of Formula C under reaction conditions:

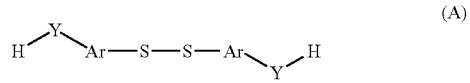

(A)

(B)

(C)

thereby preparing the polymer of Formula III, wherein,

Ar, independently for each occurrence, is an aryl or heteroaryl group, such as a substituted or unsubstituted phenyl group;

U is O or S, preferably O;

X is a leaving group, such as a halogen;

Y is NR", S, or O, particularly NR", such as NH;

L is a linking group;

R" is H or lower alkyl; and m is an integer greater than 10.

In certain embodiments, the reaction conditions comprise a base, such as an amine base, for example, pyridine.

In some embodiments, the reaction conditions comprise a polar organic solvent, such as a polar aprotic organic solvent, such as acetonitrile, DMSO, DMF, or N-methylpyrrolidinone (NMP), particularly N-methylpyrrolidinone (NMP).

BRIEF DESCRIPTION OF THE DRAWINGS

The following figures depict illustrative embodiments of the invention. These depicted embodiments are to be understood as illustrative of the invention and not as limiting in any way.

DETAILED DESCRIPTION OF THE INVENTION

1. Definitions

Figure 1A:
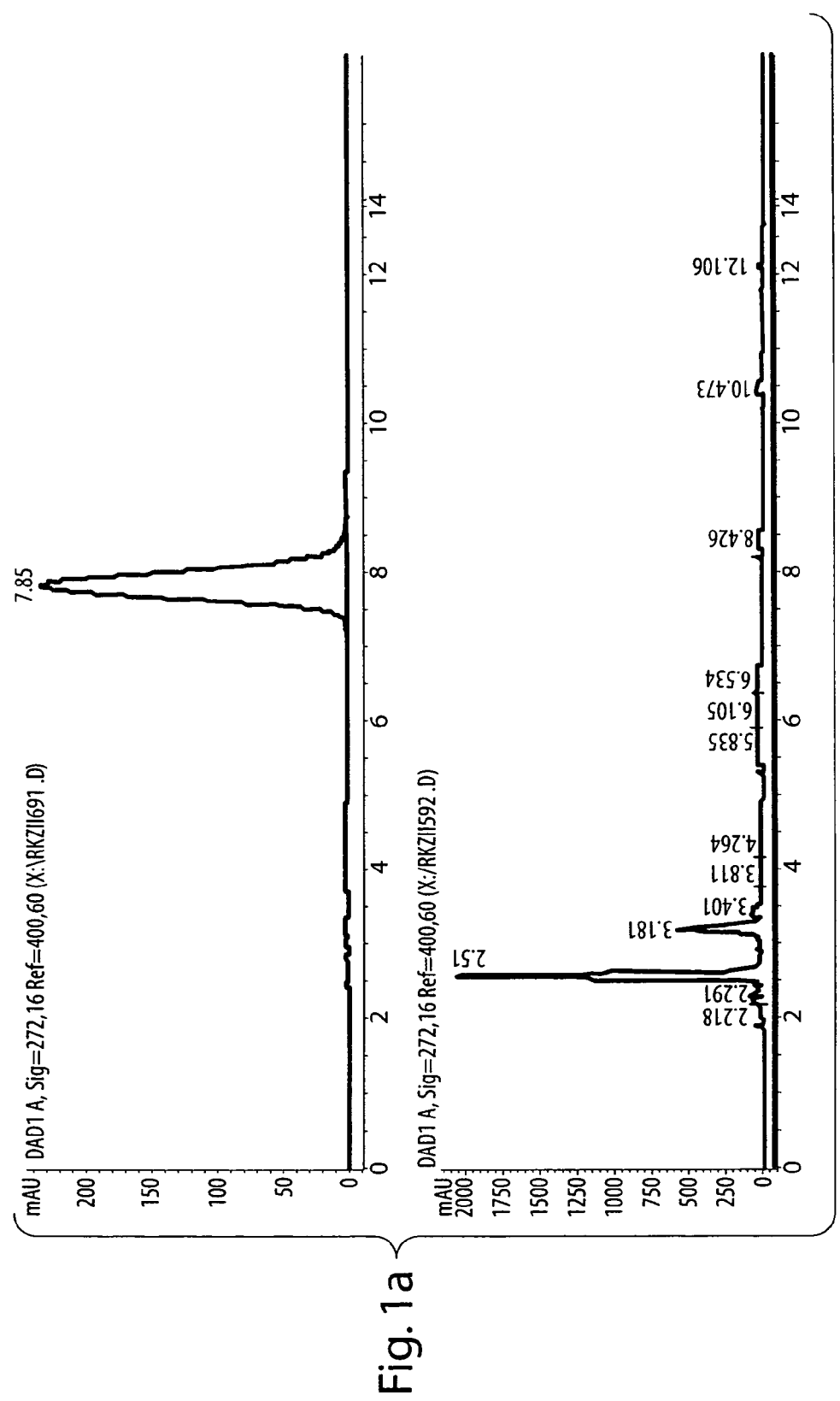
FIGS. 1a-1b depict HPLC and mass spectral data, respectively, for the degradation of 4-aminophenyl disulfide.

For convenience, before further description of the present invention, certain terms employed in the specification, examples, and appended claims are collected here. These definitions should be read in light of the remainder of the disclosure and understood as by a person of skill in the art.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure. Alkyl also includes, where appropriate, divalent alkyl groups, i.e. "alkylene" groups.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below.

Cycloalkyls can be further substituted with alkyls, alkenyls, alkoxys, alkylthios, aminoalkyls, carbonyl-substituted alkyls, —$CF_3$, —CN, and the like.

The term "$C_{x\text{-}y}$" when used in conjunction with a chemical moiety, such as, acyl, acyloxy, alkyl, alkenyl, alkynyl, or alkoxy is meant to include groups that contain from x to y carbons in the chain. For example, the term "$C_{x\text{-}y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2\text{-}y}$alkenyl" and "$C_{2\text{-}y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

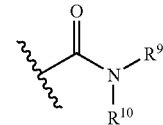

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

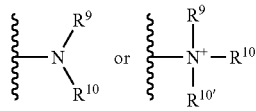

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

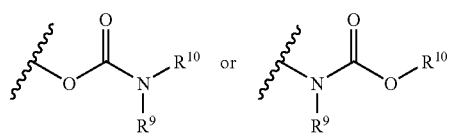

wherein $R^9$ and $R^{10}$ independently represent hydrogen or a hydrocarbyl group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —$OCO_2$—$R^9$, wherein $R^9$ represents a hydrocarbyl group.

The term "carboxy", as used herein, refers to a group represented by the formula —$CO_2H$.

The term "ester", as used herein, refers to a group —C(O)O$R^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, alkyleneamine (such as ethyleneamine), 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "leaving group", as used herein refers to a group capable of being displaced from an electrophilic atom on attack by a nucleophilic atom. Examples include halogens (e.g., F, Cl, Br, or I), alkylthio, cyano, alkoxy, sulfonates (e.g. triflate, mesylate, nosylate, tosylate, etc.) acyl, and other recognized or predictable by knowledge available in the art.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkyl, an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

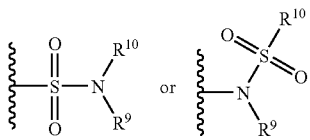

wherein $R^9$ and $R^{10}$ independently represents hydrogen or hydrocarbyl.

The term "sulfoxide" is art-recognized and refers to the group —S(O)—$R^9$, wherein $R^9$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^9$, wherein $R^9$ represents a hydrocarbyl.

The term "thioalkyl", as used herein, refers to an alkyl group substituted with a thiol group.

The term "thioester", as used herein, refers to a group —C(O)S$R^9$ or —SC(O)$R^9$ wherein $R^9$ represents a hydrocarbyl.

The term "thioether", as used herein, is equivalent to an ether, wherein the oxygen is replaced with a sulfur.

The term "urea" is art-recognized and may be represented by the general formula

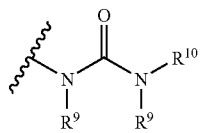

wherein $R^9$ and $R^{10}$ independently represent hydrogen or a hydrocarbyl.

The term "active" as used herein means biologically, therapeutically or pharmacologically active.

An "adjuvant," as the term is used herein, is a compound that has little or no therapeutic value on its own, but increases the effectiveness of a therapeutic agent. Exemplary adjuvants include radiosensitizers, transfection-enhancing agents (such as chloroquine and analogs thereof), chemotactic agents and chemoattractants, peptides that modulate cell adhesion and/or cell mobility, cell permeabilizing agents, inhibitors of multidrug resistance and/or efflux pumps, etc.

The term "agent" as used herein is synonymous with "at least one agent," "compound," or "at least one compound," and means at least one drug or codrug, or a prodrug thereof. In certain embodiments, the agent may be at least one low-solubility codrug, or a prodrug thereof. In certain embodiments the codrug, or prodrug thereof, is designed to have low solubility in either the core, the biological fluid or both. In certain embodiments, the agent may be a protein, peptide, or a pegylated agent. In still other embodiments, the term "agent" refers to a plurality of drugs, proteins, peptides, etc. In certain embodiments the agent may be in granular form. In certain embodiments, the agent may be combined with a pharmaceutically acceptable carrier. In certain embodiments, the agent is in liquid form.

The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes inflammation or irritation, or induces an immune reaction, in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37° C. until complete degradation is observed. The solution is then neutralized with 1 M HCl. About 200 µL of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

The term "biodegradable" is synonymous with "bioerodible" and is art-recognized. It includes polymers, compositions and formulations, such as those described herein, that degrade during use over long periods of time, e.g. days, weeks, months, years. Biodegradable polymers typically differ from non-biodegradable polymers in that the former may degrade during use. In general, degradation attributable to biodegradability involves the degradation of a biodegradable polymer into its component subunits, or digestion, e.g., by a biochemical process, of the polymer into smaller, non-polymeric subunits. For the purposes of the present disclosure, biodegradation does not include polymer degradation initiated by one or more triggers as described herein.

The term "delivery agent" is an art-recognized term, and includes molecules that facilitate the intracellular delivery of a therapeutic agent or other material. Examples of delivery agents include: sterols (e.g., cholesterol) and lipids (e.g., a cationic lipid, virosome or liposome).

The term "drug delivery device" is an art-recognized term and refers to any medical device suitable for the application of a drug or therapeutic agent to a targeted organ or anatomic region. The term includes, without limitation, those formulations of the compositions of the present invention that release the therapeutic agent into the surrounding tissues of an anatomic area.

When used with respect to a therapeutic agent or other material, the term "sustained release" is art-recognized. For example, a subject composition which releases a substance over time may exhibit sustained release characteristics, in contrast to a bolus type administration in which the entire amount of the substance is made biologically available at one time. For example, in particular embodiments, upon contact with body fluids including blood, spinal fluid, lymph or the like, the polymer matrices (formulated as provided herein and otherwise as known to one of skill in the art) may undergo gradual degradation (e.g., through hydrolysis) with concomitant release of any material incorporated therein, e.g., an therapeutic and/or biologically active agent, for a sustained or extended period (as compared to the release from a bolus). This release may result in prolonged delivery of therapeutically effective amounts of any incorporated therapeutic agent. Sustained release will vary in certain embodiments as described in greater detail below.

An "effective amount" or "therapeutically effective amount" of an agent, with respect to methods of treatment, refers to an amount of the agent in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose. A therapeutically effective amount, as recognized by those of skill in the art, will be determined on a case by case basis. Factors to be considered include, but are not limited to, the disorder to be treated and the physical characteristics of the one suffering from the disorder.

As used herein, the term "$EC_{50}$" means the concentration of a drug that produces 50% of its maximum response or effect.

As used herein, the term "$ED_{50}$" means the dose of a drug that produces 50% of its maximum response or effect.

The terms "encapsulated" is art-recognized when used in reference to a therapeutic agent, or other material and a polymeric composition, such as a composition of the present invention. In certain embodiments, these terms include incorporating, formulating, or otherwise including such agent into a composition that allows for release, such as sustained release, of such agent in the desired application. The terms contemplate any manner by which a therapeutic agent or other material is incorporated into a polymer matrix, including for example: attached to a monomer of such polymer (by covalent, ionic, or other binding interaction), physical admixture, enveloping the agent in a coating layer of polymer, having such monomer be part of the polymerization to give a polymeric formulation, appended to the surface of the polymeric matrix (by covalent or other binding interactions), etc.

The term "co-incorporation" or "co-encapsulation" refers to the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer of the invention that it is dispersed as small droplets, rather than being dissolved, in the polymer. Any form of encapsulation or incorporation is contemplated by the present invention, in so much as the release, preferably sustained release, of any encapsulated therapeutic agent or other material determines whether the form of encapsulation is sufficiently acceptable for any particular use.

The term "fiber" as used herein, refers to a slender, elongated, wire-like object or structure. "Fiber" and "filament" are used interchangeably herein. A fiber of the present invention refers to a degradable polymer with a slender, elongated shape. In certain embodiments, "fiber" as used herein, also includes one or more sections which possess a ribbon configuration comprising a flexible, flat and/or thin profile or shape. In some embodiments, "fiber" as used herein also includes one or more tube configurations; that is, elongated structures with a hollow core at their centers, for example, tube-like structures. As such, a fiber of the present invention may also refer to a degradable polymer tube, i.e., a fiber fashioned to include a hollow portion in its center, such as a longitudinally extending lumen. In certain embodiments, a fiber comprises portions that have different physical characteristics and or configurations, e.g., ribbon portions, hollow portions, bulb portions, or different chemical characteristics, e.g., polymers or polymer blends, additives, or the like.

The term "$IC_{50}$" means the dose of a drug that inhibits a biological activity by 50%.

The term "$LD_{50}$" means the dose of a drug that is lethal in 50% of test subjects.

A "patient," "subject," or "host" to be treated by the subject method may mean either a human or non-human animal, such as primates, mammals, and vertebrates.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filter, diluent, excipient, solvent or encapsulating material suitable for formulating a medical or cosmetic composition. Each carrier must be "acceptable" in the sense of being compatible with other ingredients of the formulation and not injurious to the patient.

Some examples of materials which can serve as pharmaceutically acceptable carriers include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions, including without limitation, analgesic agents, therapeutic agents, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.* 66: 1-19 (1977).

"Physiological conditions" describe the conditions inside an organism, i.e., in vivo. Physiological conditions include the acidic and basic environments of body cavities and organs, enzymatic cleavage, metabolism, and other biological processes, and preferably refer to physiological conditions in a vertebrate, such as a mammal.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The phrase "protecting group" or "protective group" as used herein means a temporary substituent that protects a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

As used herein, the term "RNAi construct" is a generic term including small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

The phrase "substantially degrades" or "substantial degradation" as used herein refers to the rapid cleavage of one or more types of chemical bonds in the backbone of the present polymers, converting polymer molecules into shorter monomers and/or oligomers. Substantial degradation can be observed by several means, for example, by a decrease in the average molecular weight of the polymer, attributable to the conversion of individual polymer molecules into smaller fragments. Substantial degradation can also be observed by a loss of bulk physical properties associated with the polymer but not with the corresponding monomers or oligomers or with smaller fragments derived from degradation of the polymer, for example, change in a composition comprising the polymer from solid to liquid (or vice versa) or a change in the hardness of the composition. In some embodiments, substantial degradation can be observed by a decrease in hardness, for example, by an increase in the malleability and/or pliability of the polymer. A change in viscosity, if the polymer or composition thereof is liquid, can also be associated with substantial degradation. For example, in some embodiments, the viscosity of the polymer decreases with substantial degradation, such as by about 10%, 20%, 50%, 70% or more. In other embodiments, the viscosity of the polymer increases similarly with substantial degradation. Moreover, the cleavage of one or more chemical bonds in the backbone of the polymer undergoing substantial degradation occurs rapidly. For example, upon triggering substantial degradation, one or more of the above physical characteristics of the polymer may undergo such change within about five hours, two hours, or one hour, preferably, less than about thirty minutes, fifteen minutes, or five minutes, more preferably less than about one minute, or less than about 10 seconds. For example, upon triggering substantial degradation, the polymer may have a half-life less than about five hours, two hours, or one hour, preferably, less than about thirty minutes, fifteen minutes, or five minutes, more preferably less than about one minute, or less than about 10 seconds. In another example, on triggering substantial degradation in a given sample of polymer, over 10%, 20%, 30%, or 50% of polymer molecules are cleaved in one or more places within one hour or thirty, fifteen or five minutes or less, preferably within 2 minutes or less, or in less than one minute. In preferred embodiments, on triggering substantial degradation, over 20%, 50%, 70%, or 90% of occurrences of a cleavable bond within a given polymer molecule are cleaved within one hour or thirty, fifteen or five minutes or less, preferably within 2 minutes or less, or in less than one minute.

General decomposition of polymers through exposure to environmental factors not associated with one or more triggers is not considered "substantial degradation." For example, gradual polymer degradation such as biodegradation or bioerosion is not considered "substantial degradation." Generally, degradations of polymers that are slow, e.g., wherein the polymer half life is greater than about one hour, are not considered "substantial degradation" for the purposes of the present invention.

The phrases "systemic administration," "administered systemically," "peripheral administration" and "administered peripherally" are art-recognized, and include the administration of a subject composition, therapeutic or other material at a site remote from the disease being treated. Administration of an agent directly into, onto, or in the vicinity of a lesion of the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

The term "therapeutic index" refers to the therapeutic index of a drug defined as $LD_{50}/ED_{50}$.

The term "thread" as used herein includes one or more fibers or filaments, at least one of which may be a biodegradable drug-containing fiber of the present invention. When a thread comprises more than one fiber, the fibers may be twisted, interwoven, spun, tufted, or otherwise braided together to form the thread. Thus, threads of the present invention include monofilaments, braided polyfilaments, and other associations of multiple fibers. The systems and methods described herein are amenable to the use of the present threads and/or fibers, unless specifically stated to the contrary. For example, in some embodiments, threads may also possess one or more ribbon configurations and/or tube configurations.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "trigger" as used herein refers to one or more external stimuli applied at a specified and controlled time that initiate substantial degradation of the polymers described herein. In some instances, one or more triggers do not initiate substantial degradation of one or more polymers in the absence of one or more additional triggers; that is, in some embodiments, substantial degradation of the polymer does not initiate until the polymer has been exposed to two or more triggers. Typically, one or more triggers are applied from an external source, i.e., from a source exogenous to the location of the polymer. External application of one or more triggers often serves to avoid unintended or premature initiation of the substantial degradation of the polymer.

2. Polymers

The compositions, systems, and methods described herein generally relate to a biocompatible polymer, wherein the polymer substantially degrades in the presence of one or more triggers, preferably light energy or hydrogen peroxide, but does not substantially degrade in the absence of one or more triggers. For example, in preferred embodiments, the polymer does not substantially degrade under physiological conditions in the absence of one or more triggers.

In certain embodiments, the polymer substantially degrades through the cleavage of carbon-carbon bonds, carbon-oxygen bonds, carbon-nitrogen bonds, carbon-boron bonds, nitrogen-nitrogen bonds, sulfur-sulfur bonds, boron-oxygen bonds, oxygen-phosphorous bonds, or a combination thereof. In some embodiments, the bonds that are cleaved are substantially in the backbone of the polymer. In preferred embodiments, the polymer substantially degrades through the cleavage of carbon-carbon bonds, carbon-oxygen bonds, carbon-boron bonds, sulfur-sulfur bonds, boron-oxygen bonds, or a combination thereof. In preferred cases, the particular polymer bonds cleaved are selected by appropriate choice of one or more triggers. For example, one or more triggers may be selected such that carbon-oxygen bonds are cleaved, but carbon-carbon bonds are not cleaved.

In some instances, the polymer is composed of more than one type of a bond comprising a given pair of atoms, for example, more than one type of carbon-carbon bond, such as an alkyl-alkyl bond and an aryl-alkyl bond. The present invention contemplates the selective cleavage of a given type of bond comprising a specific pair of atoms in the presence of another different bond containing the same pair of atoms. For example, in some embodiments the sulfur-sulfur bond in an aryl-S—S-aryl moiety may be cleaved in the presence of the sulfur-sulfur bond in an alkyl-S—S-alkyl or aryl-S—S-alkyl moiety.

In some embodiments, the polymer substantially degrades through the cleavage of carbon-carbon bonds, carbon-oxygen bonds, or sulfur-sulfur bonds, and at least one trigger is light energy. The light energy may be selected by adjusting its frequency or wavelength to be of sufficient energy to cleave carbon-carbon bonds, carbon-oxygen bonds, or sulfur-sulfur bonds. The light energy may be selected to cleave only one of carbon-carbon bonds, carbon-oxygen bonds, or sulfur-sulfur bonds in the presence of other bonds. The light energy may be further selected to cleave only one type of one carbon-carbon bonds, carbon-oxygen bonds, or sulfur-sulfur bonds in the presence of other bonds. Alternatively, the light energy may be selected to cleave more than one bond type comprising a given pair of atoms. In other embodiments, the light energy is selected to cleave more than one bond type comprising different pairs of atoms.

In other embodiments, the polymer substantially degrades through the cleavage of carbon-boron bonds and optionally boron-oxygen bonds, and at least one trigger is hydrogen peroxide. The concentration of hydrogen peroxide can be selected to modulate the rates of cleavage and to select for cleavage of specific bonds.

In some embodiments, the polymer comprises carbon-boron bonds and optionally boron-oxygen bonds in the backbone of the polymer. For example, the carbon-boron bonds in the backbone may be $sp^2$ carbon-boron bonds, such as aryl-boron, heteroaryl-boron, or alkenyl-boron bonds. In other instances the carbon-boron bonds in the backbone are $sp^3$ carbon-boron bonds, such as alkyl-boron bonds. In further embodiments the carbon-boron bonds in the backbone are sp carbon-boron bonds, such as alkynyl-boron bonds. Additionally, in some embodiments the carbon-boron bonds in the backbone comprise a combination of sp² carbon-boron, sp³ carbon-boron, and/or sp carbon-boron bonds.

In certain embodiments, the boron atoms of the carbon-boron bonds in the backbone of the polymer have the substitution:

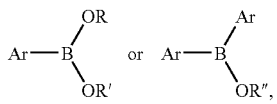

wherein,

Ar is an aryl or heteroaryl moiety that is part of the polymer backbone;

R is an alkyl moiety that is part of the polymer backbone;

R' is H, lower alkyl, or an alkyl moiety that is part of the polymer backbone; and R" is H or lower alkyl, wherein optionally R and R' together with any intervening atoms form a 5- to 7-membered ring.

In certain embodiments, Ar is a substituted aryl ring, such as a substituted benzene ring. For example, a di-substituted benzene ring wherein each of the two substitutions is the polymer backbone. In some instances, the polymer backbone may attach to Ar by carbonyl linkages, such as ester, amide, thioester, urea, carbonate, urethane linkages particularly ester or amide linkages. In certain embodiments, the polymer backbone may attach to Ar by alkyl, alkenyl, alkynyl, or hydrocarbyl linkages.

In embodiments where applicable, attachment points of the polymer backbone to Ar may occur in a 1,4-, 1,2-, or 1,3- relationship, particularly in a 1,4-relationship.

In addition to being attached to the backbone, Ar may be further substituted, for example with groups not part of the polymer backbone. Substituents may include one or more of halogen, nitro, cyano, hydroxyl, thiol, carboxyl, sulfate, substituted or unsubstituted amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, alkyl, alkenyl, alkynyl, acyl, acyloxy, acylamino, aryl, heteroaryl, carbocyclyl, heterocyclyl, aralkyl, hetaralkyl, carbocyclylalkyl, and heterocyclylalkyl.

In some embodiments, the moiety —B(OR)(OR') may comprise a 5- to 7-membered ring wherein the boron atom and two oxygen atoms are part of the ring and both R and R' for the remainder of the ring. For example, the moiety —B(OR)(OR') may form a substituted or unsubstituted 1,3,2-dioxaborolane ring, a substituted or unsubstituted 1,3,2-dioxaborinane ring, or a substituted or unsubstituted 1,3,2-dioxaborepane ring.

In some embodiments, the polymer has a structure represented according to Formula I:

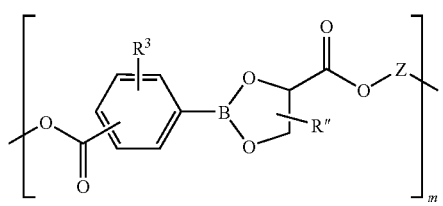

(I)

wherein

R³ is one or more occurrences of H, halogen, nitro, cyano, hydroxyl, thiol, carboxyl, sulfate, substituted or unsubstituted amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, alkyl, alkenyl, alkynyl, acyl, acyloxy, acylamino, aryl, heteroaryl, carbocyclyl, heterocyclyl, aralkyl, hetaralkyl, carbocyclylalkyl, and heterocyclylalkyl;

R" is H or lower alkyl;

Z is a comonomer, such as a diamine-containing monomer; and m is an integer greater than 10.

In some embodiments, Z is a comonomer suitable for forming a polymer with another monomer bearing two carboxylic acid groups. For example, in some embodiments, Z is a diamine-containing monomer, such as an alkylenediamine (such as ethylenediamine) or an aryldiamine (such as diaminobenzene). In other embodiments, Z is a dihydroxy-containing monomer, such as an alkylenediol (such as ethylene glycol) or an aryldiol (such as hydroquinone).

In other embodiments, the backbone of the polymer comprises one or more occurrences of the structure:

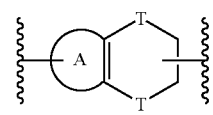

wherein

A is an aryl or heteroaryl ring that is part of the polymer backbone;

T is CR"₂ or O, preferably O; and wherein the ring containing both T groups is optionally further substituted and is part of the polymer backbone.

In certain embodiments, A is a substituted aryl ring, such as a substituted benzene ring. In some instances, the polymer backbone may attach to A by carbonyl linkages, such as ester, amide, thioester, urea, carbonate, urethane linkages. In certain embodiments, the polymer backbone may attach to A by alkyl, alkenyl, alkynyl, or hydrocarbyl linkages.

In addition to being attached to the backbone, A may be further substituted, for example with groups not part of the polymer backbone. Substituents may include one or more of halogen, nitro, cyano, hydroxyl, thiol, carboxyl, sulfate, substituted or unsubstituted amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, alkyl, alkenyl, alkynyl, acyl, acyloxy, acylamino, aryl, heteroaryl, carbocyclyl, heterocyclyl, aralkyl, hetaralkyl, carbocyclylalkyl, and heterocyclylalkyl.

In some instances, the polymer backbone may attach to the ring containing both T groups by carbonyl linkages, such as ester, amide, thioester, urea, carbonate, urethane linkages, particularly ester or amide linkages. In certain embodiments, the polymer backbone may attach to A by alkyl, alkenyl, alkynyl, or hydrocarbyl linkages.

In addition to being attached to the backbone, the ring containing both T groups may be further substituted, for example with groups not part of the polymer backbone. Substituents may include one or more of halogen, nitro, cyano, hydroxyl, thiol, carboxyl, sulfate, substituted or unsubstituted amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, alkyl, alkenyl, alkynyl, acyl, acyloxy, acylamino, aryl, heteroaryl, carbocyclyl, heterocyclyl, aralkyl, hetaralkyl, carbocyclylalkyl, and heterocyclylalkyl, particularly alkyl.

In some embodiments, the polymer has a structure represented according to Formula II:

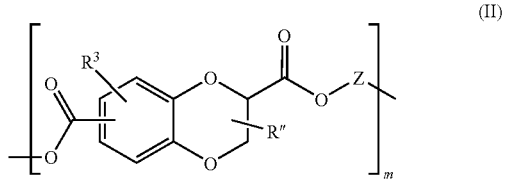

wherein, $R^3$ is one or more occurrences of H, halogen, nitro, cyano, hydroxyl, thiol, carboxyl, sulfate, substituted or unsubstituted amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, alkyl, alkenyl, alkynyl, acyl, acyloxy, acylamino, aryl, heteroaryl, carbocyclyl, heterocyclyl, aralkyl, hetaralkyl, carbocyclylalkyl, and heterocyclylalkyl;

R″ is H or lower alkyl;

Z is a comonomer, such as a diamine-containing monomer; and m is an integer greater than 10.

In some embodiments, Z is a comonomer suitable for forming a polymer with another monomer bearing two carboxylic acid groups. For example, in some embodiments, Z is a diamine-containing monomer, such as an alkylenediamine (such as ethylenediamine) or an aryldiamine (such as diaminobenzene). In other embodiments, Z is a dihydroxy-containing monomer, such as an alkylenediol (such as ethylene glycol) or an aryldiol (such as hydroquinone).

In some embodiments, the backbone of the polymer comprises one or more occurrences of the structure:

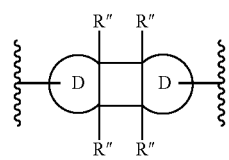

wherein,

D is a carbocyclyl or heterocyclyl ring that is part of the polymer backbone; and R″, independently for each occurrence, is H or lower alkyl.

In certain embodiments, the polymer substantially degrades through one or more electrocyclic or retro-cycloaddition reactions, for example, retro-[2+2]cycloaddition reactions or retro-Diels-Alder reactions. For example, the polymer may substantially degrade through a retro-cycloaddition reaction, such as a retro-[2+2]cycloaddition reaction in the presence of a trigger, wherein the trigger is light energy, for example, light energy having a wavelength of between about 250 and 260 nm, such as about 254 nm.

In other embodiments, the polymer substantially degrades through homolytic cleavage of one or more chemical bonds.

In further embodiments, the polymer of substantially degrades through oxidation of atoms of the polymer, for example, in the polymer backbone.

In some embodiments, the polymer substantially degrades in the presence of both a first and second trigger; but the polymer does not substantially degrade in the presence of either the first or second trigger alone. In such embodiments, the polymer may substantially degrade through the cleavage of carbon-carbon bonds, carbon-oxygen bonds, carbon-nitrogen bonds, carbon-boron bonds, nitrogen-nitrogen bonds, sulfur-sulfur bonds, boron-oxygen bonds, oxygen-phosphorous bonds, or a combination thereof. In preferred embodiments, the polymer substantially degrades through the cleavage of carbon-oxygen bonds, carbon-boron bonds, sulfur-sulfur bonds, boron-oxygen bonds, or a combination thereof.

In certain embodiments, the first or second trigger is light energy, for example, light energy of a suitable wavelength to induce homolytic cleavage of one or more chemical bonds of the polymer or to induce one or more monomers of the polymer to undergo a retrocycloaddition reaction. In other embodiments, the first or second trigger is hydrogen peroxide, and one or more atoms of the polymer may undergo oxidation.

In certain embodiments, the polymer substantially degrades through the cleavage of sulfur-sulfur bonds and the first trigger is light energy and the second trigger is hydrogen peroxide. In some embodiments, light energy has a wavelength in the ultraviolet region, for example a wavelength of between about 200 and 300 nm, such as between about 250 and 270 nm, such as about 260 nm or about 266 nm. In such instances, it is preferable that the polymer comprises sulfur-sulfur bonds in the backbone of the polymer. For example, the polymer may comprise substituted or unsubstituted bis(aminoaryl)-disulfide monomers, such as substituted or unsubstituted bis(4-aminophenyl)-disulfide monomers.

In some embodiments, the polymer further comprises substituted or unsubstituted monomers or comonomers that do not contain bonds which undergo cleavage the presence of one or more triggers. For example, in certain embodiments, the polymer further comprises substituted or unsubstituted hydrocarbylene diacid monomers, such as PEG diacid monomers or alkylene diacid monomers, such as adipic acid monomers. Further examples include alkylene diacid monomers, such as terephthalic acid monomers.

In some embodiments, the polymer has a structure represented according to Formula III:

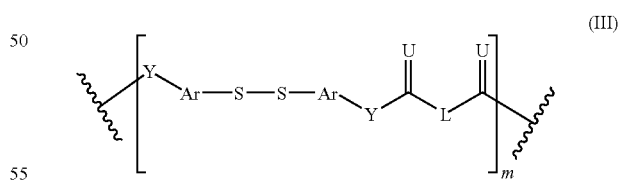

wherein,

Ar, independently for each occurrence, is an aryl or heteroaryl group, such as a substituted or unsubstituted phenyl group;

U is O or S, preferably O;

Y is NR″, S, or O, particularly NR″, such as NH;

L is a linking group;

R″ is H or lower alkyl; and m is an integer greater than 10.

For the purposes of the present invention, L can represent a large variety of moieties, such as any linking group known in the art that does not interfere with the substantial degradation of the polymer. In certain embodiments, L is a hydrocarbyl group. For example, in some instances, L is alkyl, such as alkylene. For instance, in some embodiments, L is $M_n$, wherein n is an integer from 0 to 20, for example, 2, 3, 4, 5, or 6, particularly 4, wherein M, independently for each occurrence, is substituted or unsubstituted methylene. In some embodiments, M is unsubstituted methylene for each occurrence. In some embodiments, L is alkyl wherein one or more carbon atoms in the main chain are replaced by a heteroatom, such as O, S, or NR", for example ethyl-oxy-ethyl, PEG, —O—CH$_2$—CH$_2$-PEG-CH$_2$—CH$_2$—O—, etc. In some examples, L includes one or more aryl or heteroaryl rings, such as substituted or unsubstituted phenyl, aralkyl, heteroaryl, heteroaralkyl.

3. Methods of Polymer Degradation

The present invention also contemplates a method for the degradation of a polymer in a patient, comprising:

a) subjecting the polymer to an amount of a first trigger; and b) subjecting the polymer to an amount of a second trigger in the presence of the first trigger;

thereby degrading the polymer in the patient, wherein the polymer substantially degrades in the presence of both the first and second trigger, and the polymer does not substantially degrade in the presence of either the first or second trigger alone.

The present methods contemplate polymers in the form of solids, solutions, liquids, and/or films.

In some embodiments, the first trigger is light energy and the second trigger is hydrogen peroxide. Alternatively, the first trigger may be hydrogen peroxide and the second trigger may be light energy.

In certain embodiments, the polymer of the present method substantially degrades through the cleavage of carbon-carbon bonds, carbon-oxygen bonds, carbon-nitrogen bonds, carbon-boron bonds, nitrogen-nitrogen bonds, sulfur-sulfur bonds, boron-oxygen bonds, oxygen-phosphorous bonds, or a combination thereof, particularly through the cleavage of sulfur-sulfur bonds.

In some embodiments, wherein the first trigger is light energy and the second trigger is hydrogen peroxide, the light energy is of a suitable wavelength to induce homolytic cleavage of one or more sulfur-sulfur bonds of the polymer, and such sulfur-sulfur bonds may be part of the backbone of the polymer. In some embodiments, the hydrogen peroxide is present at a concentration compatible with biological systems, for example, such that cells are not harmed in its presence. In preferred embodiments, the light energy has a wavelength in the ultraviolet region, for example, between about 200 and 300 nm, such as between about 250 and 270 nm, for example about 260 nm or about 266 nm.

In some embodiments, the invention comprises a method for the degradation of a polymer in a patient, wherein the polymer has a structure represented according to Formula III:

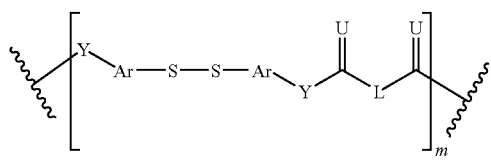

(III)

wherein

Ar, independently for each occurrence, is an aryl or heteroaryl group, such as a substituted or unsubstituted phenyl group;

U is O or S, preferably O;

Y is NR", S, or O, particularly NR", such as NH;

L is a linking group;

R" is H or lower alkyl; and m is an integer greater than 10.

In other embodiments, the present methods comprise steps for the degradation of a polymer not in a patient. Such polymers may be in the form of solids, solutions, liquids, and/or films.

4. Implants

The present invention also contemplates a biocompatible implant comprising one or more polymers and/or composition(s) of polymers as described herein. In some embodiments, the implant is a suture and/or a clip, for example for holding tissue in place in a patient. In other embodiments, the implant is a partition for separating or dividing tissues in the body of a patient. In certain embodiments, the implant is a stent.

In certain embodiments, the implant is temporary, and it is removed by substantially degrading the polymer through exposure to one or more triggers.

5. Coatings and Compositions

The present invention also contemplates coatings comprising one or more polymers and/or composition(s) of polymers as described herein. In some embodiments, the coating is an adhesive, such as an adhesive suitable for oral applications.

In certain embodiments, the coating is an adhesive suitable for oral applications such as dental applications, for example, dental applications that comprise permanent or temporary fixation of a natural or synthetic tooth or tooth component.

In some embodiments, the oral applications comprise orthodontic applications, such as temporary fixation of a device or structure to a tooth, such as one or more spacers and/or braces. For example, in one embodiment, a temporary orthodontic device, fixated at an implant location, such as a tooth, by an adhesive comprising one or more of the present polymers, is removed from the implant location on substantial degradation of the polymer through exposure to one or more triggers.

In certain embodiments, the coating is a barrier, for example to separate environments on either side of the coating. For example, the coating may serve as a protective shell, sphere, or capsule, enclosing a core comprising a therapeutic agent or composition comprising a therapeutic agent for delivery to a site within a patient. The coating may protect the contents of the core from the external environment until the coating reaches a desired location in the patient, at which point exposure to one or more triggers substantially degrades the coating, releasing the contents of the core.

More generally, the present invention also contemplates compositions comprising polymers and composition of polymers as described herein in combination with one or more therapeutic agents.

6. Methods of Preparation

The present invention also contemplates methods for the preparation polymers and composition of polymers as described herein. In some embodiments, the invention comprises a method for the preparation of a polymer according to Formula III:

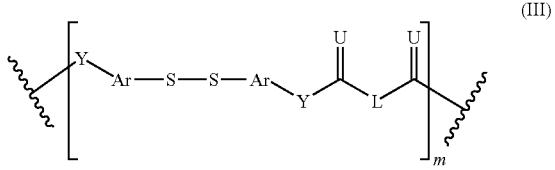

(III)

comprising reacting a monomer of Formula A with a monomer of Formula B or a monomer of Formula C under reaction conditions:

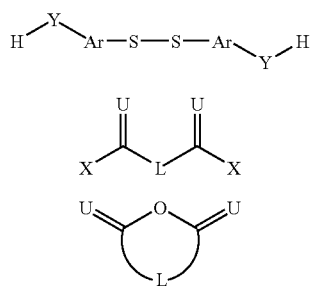

thereby preparing the polymer of Formula III, wherein

Ar, independently for each occurrence, is an aryl or heteroaryl group, such as a substituted or unsubstituted phenyl group;

U is O or S, preferably O;

X is a leaving group, such as a halogen;

Y is NR", S, or O, particularly NR", such as NH;

L is a linking group;

R" is H or lower alkyl; and m is an integer greater than 10.

In certain embodiments, the reaction conditions comprise a base, such as an amine base, for example, pyridine.

In some embodiments, the reaction conditions comprise a polar organic solvent, such as a polar aprotic organic solvent, such as acetonitrile, DMSO, DMF, N-methylpyrrolidinone (NMP), or combinations thereof, particularly N-methylpyrrolidinone (NMP). In other embodiments, the reaction conditions comprise a polar protic organic solvent, such as an alcohol, such as methanol or ethanol. In other embodiments, the reaction conditions comprise a relatively non-polar organic solvent, such as toluene, ether, petroleum ether, methylene chloride, hexanes, etc. The reaction conditions may also comprise a combination of polar aprotic, polar protic, non-polar organic solvents. The reaction conditions may also comprise aqueous solvent systems, for example, including one or more buffers. Systems involving a combination of organic and aqueous solvents are also contemplated.

In certain embodiments, the reaction conditions comprise a temperature between about 25 and 35° C., for example about ambient or room temperature or about 27° C. In other embodiments, the reaction conditions comprise a temperature greater than about 35° C., for example from about 35 to 120° C. or higher.

Variations, modifications, and other implementations of what is described herein will occur to those of ordinary skill without departing from the spirit and the scope of the invention. Accordingly, the invention is not to be limited only to the preceding illustrative description. For additional illustrative features that may be used with the invention, including the embodiments described here, refer to the documents listed herein above and incorporated by reference in their entirety. All operative combinations between the above described illustrative embodiments and those features described in U.S. Provisional Patent Application 60/638,551; as well as in Kuivila, H. G. *J. Am. Chem. Soc.* 1954, 76, 870-874; Kuivila, et al. *J. Am. Chem. Soc.* 1957, 79, 5659-5662; Letsinger et al. *J. Am. Chem. Soc.* 1959, 81, 3009-3012; Chang et al. *J. Am. Chem. Soc.* 2004, 126, 15392-15393; Mack, et al. *J. Am. Chem. Soc.* 2004, 126, 15324-15325; and Milanesi et al. *Chem. Eur. J.* 2004, 10, 1705-1710 are considered to be potentially patentable embodiments of the invention.

EXEMPLIFICATION

The invention now being generally described, it will be more readily understood by reference to the following examples which are included merely for purposes of illustration of certain aspects and embodiments of the present invention, and are not intended to limit the invention.

Degradation of 4-aminophenyl-disulfide Monomer

Figure 1B:
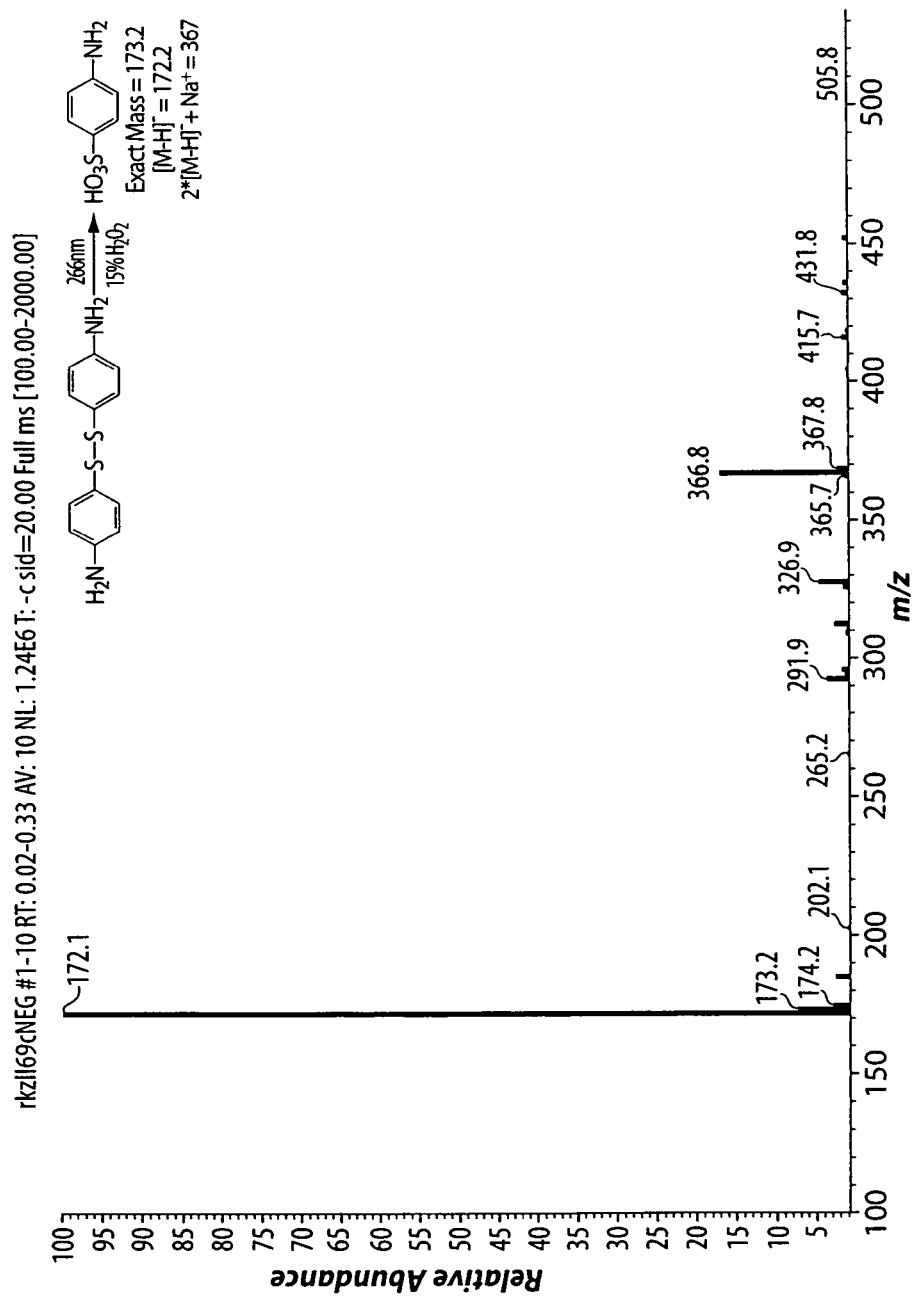

A 2 mM solution of 4-aminophenyl-disulfide was prepared in acetonitrile. 0.7 mL of this solution was then placed in a Starna quartz cuvette. To this solution was added 0.5 mL of a 15 wt % $H_2O_2$ solution followed by irradiation with 266 nm light for 1 min with mixing. The solution was then analyzed by mass spectrometry which showed formation of the degraded sulfonic acid. HPLC trace (FIG. 1a) also illustrates product fully degraded (top trace 4-aminophenyl disulfide, bottom is after irradiation). Mass spectrum (FIG. 1b) confirms degradation of the 4-aminophenyl disulfide monomer to the corresponding aminobenzene sulfonic acid.

Preparation of 4-amidophenyl-disulfide.

To a solution of 4-aminophenyl-disulfide (2.48 g, 9.99 mmole) in toluene (150 mL) was added excess acetic anhydride (1.9 mL). The resulting solution was heated at 130° C. for 1 hour. Cooled reaction to RT and a white solid precipitate formed. Collected solid by filtration, washed with toluene (3×100 mL) and dried under vacuum to obtain 4-amidophenyl-disulfide in 85% yield (2.8 g).

Degradation of 4-amidophenyl-disulfide.

Figure 2A:
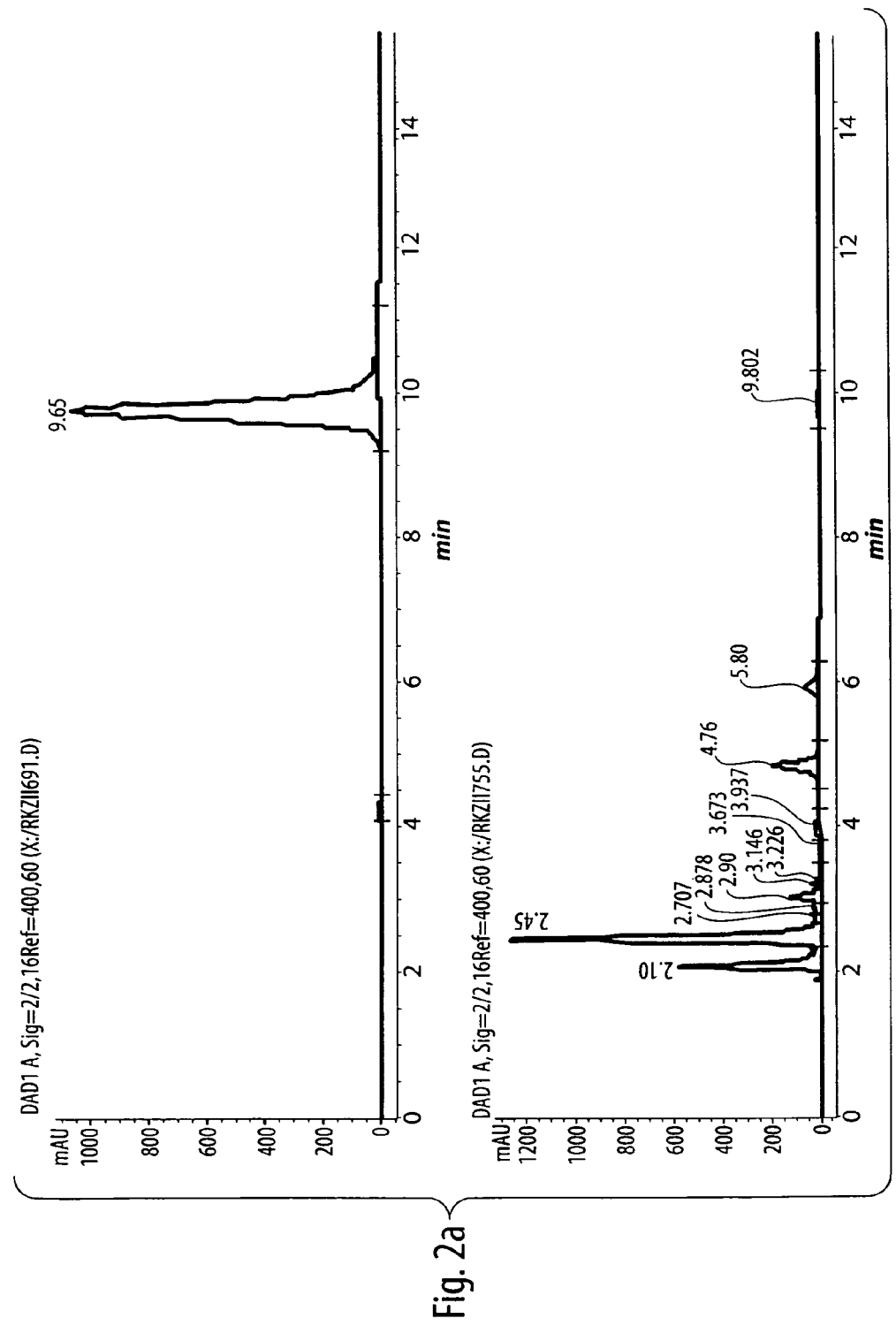
FIGS. 2a-2b depict HPLC and mass spectral data, respectively, for the degradation of 4-aminophenyl disulfide.
Figure 2B:
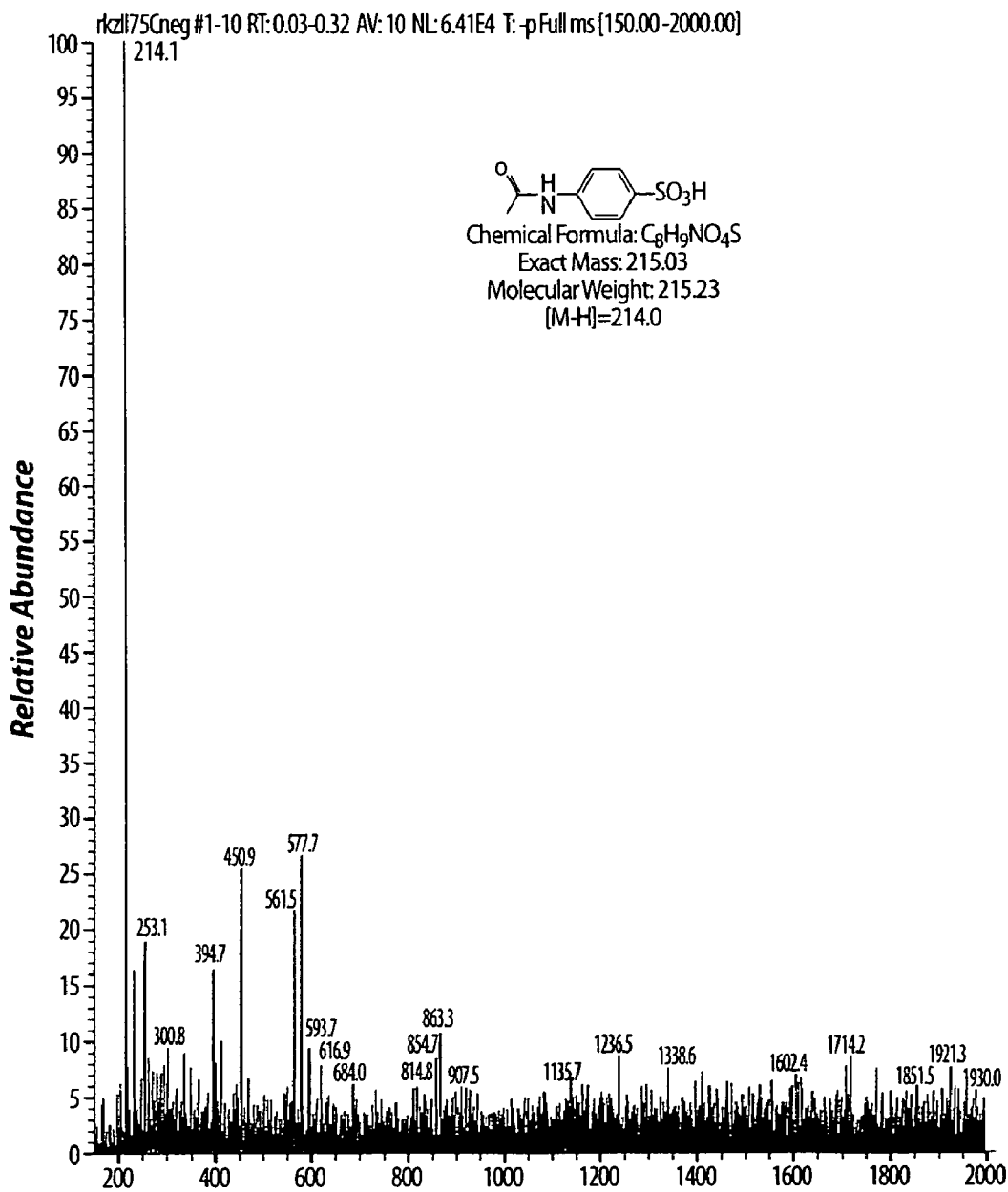

A 0.2 mM solution of 4-amidophenyl-disulfide in acetonitrile was prepared. To 0.7 mL of this solution in a quartz cuvette was added 0.5 mL 15 wt % $H_2O_2$. This solution was then irradiated at 266 nm for 1 min with mixing. The resulting solution was analyzed by HPLC (FIG. 2a, TOP: amide SM, bottom: irradiated solution) and by mass spectrometry (FIG. 2b), which confirmed degradation of the 4-amidophenyl-disulfide.

Synthesis of Adipic Dichloride Polymer Analog (1).

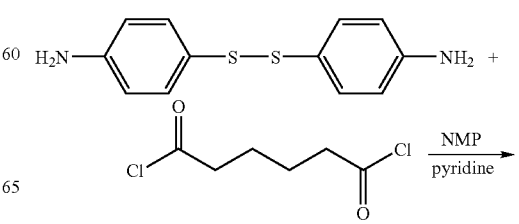

-continued

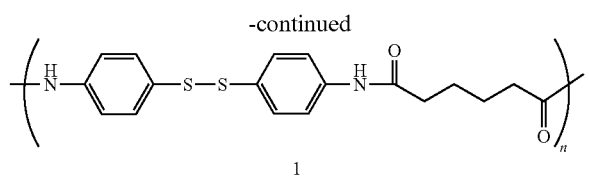

1

Figure 3A:
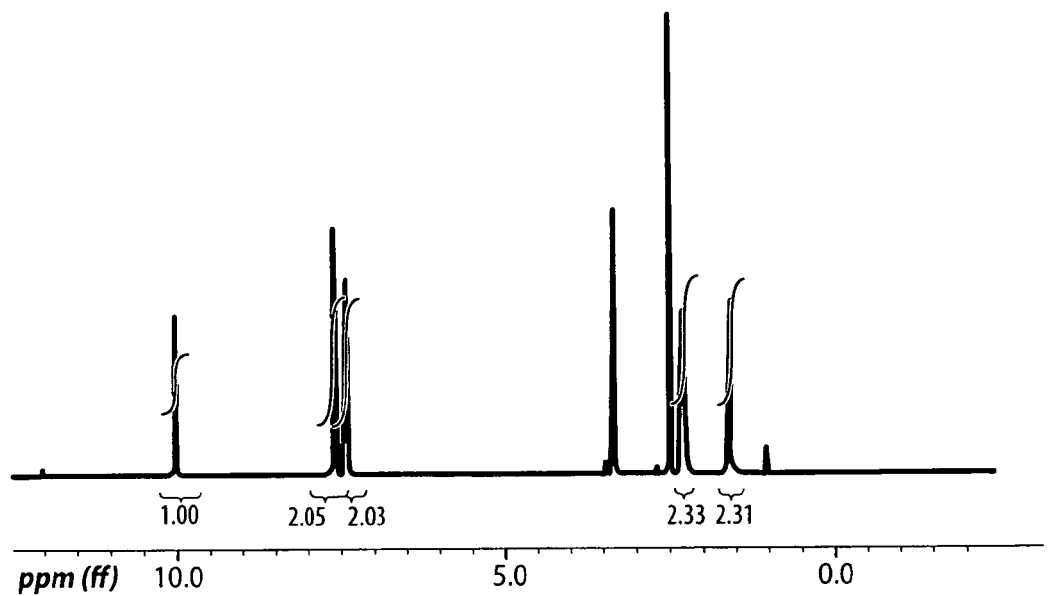
FIGS. 3a-3b depict NMR and IR data, respectively, for polymer 1.
Figure 3B:
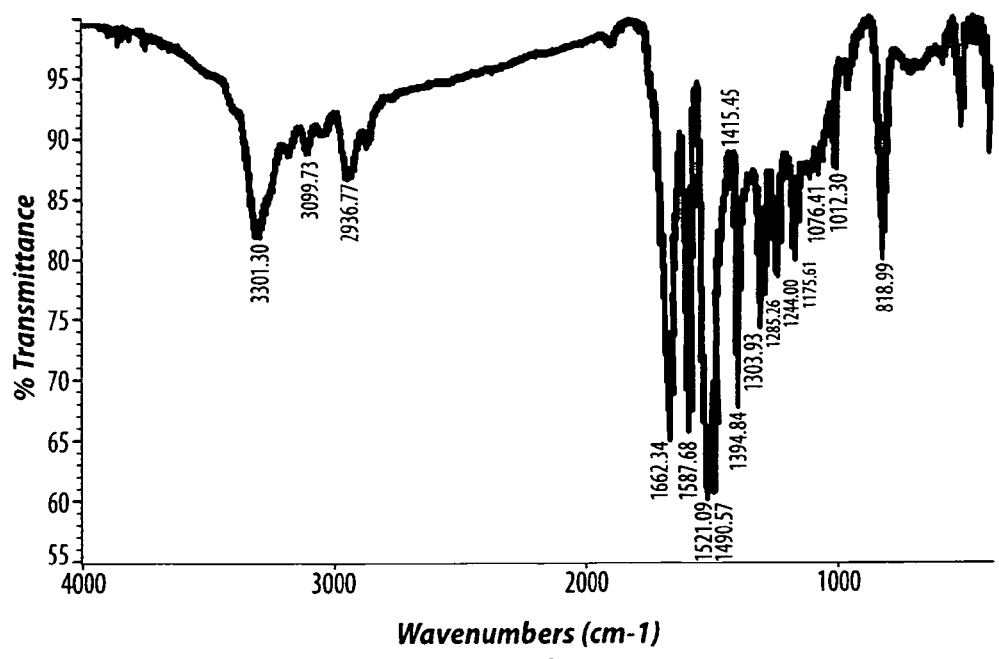

To 4-aminophenyl-disulfide (0.75 g, 3.0 mmole) was added NMP (17.5 mL) and pyridine (50 uL). This solution was stirred until fully dissolved. To this was then added adipic dichloride (0.44 mL, 3.0 mmole). The resulting solution was stirred for 6 hours at room temperature under Ar. The reaction mixture was then poured into excess EtOH (100 mL) and a white solid immediately precipitated. The white solid was collected by filtration, washed with boiling EtOH (3×100 mL) and then dried under aspirator for 12 hours. The solid product was then collected and dried under vacuum for another 12 hours. 821 mg of 1 was obtained as a solid white powder after drying. Product was characterized by $^1$H NMR in DMSO-d6 (FIG. 3a) and by infrared analysis (KBr pellet, FIG. 3b):

Synthesis of Terephthalic Dichloride Analog (2):

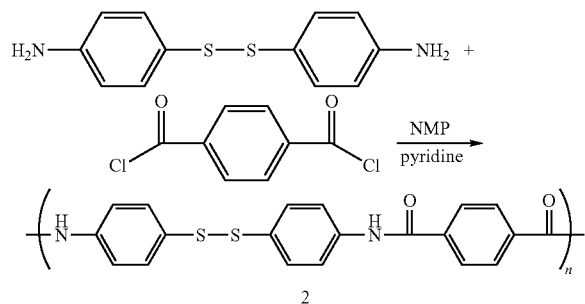

2

Figure 4A:
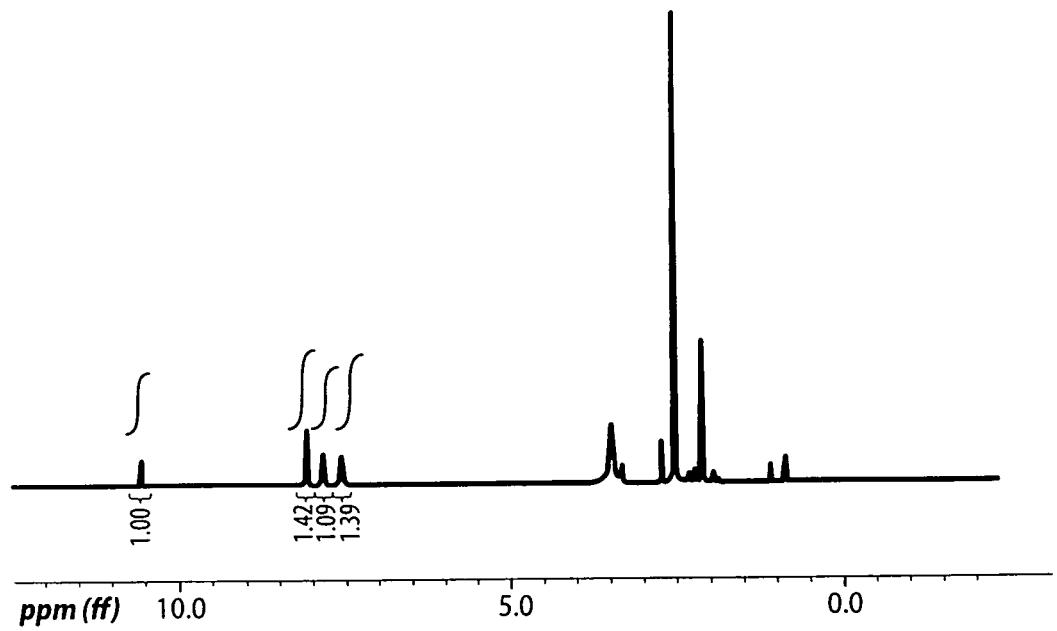
FIGS. 4a-4b depict NMR and IR data, respectively, for polymer 2.
Figure 4B:
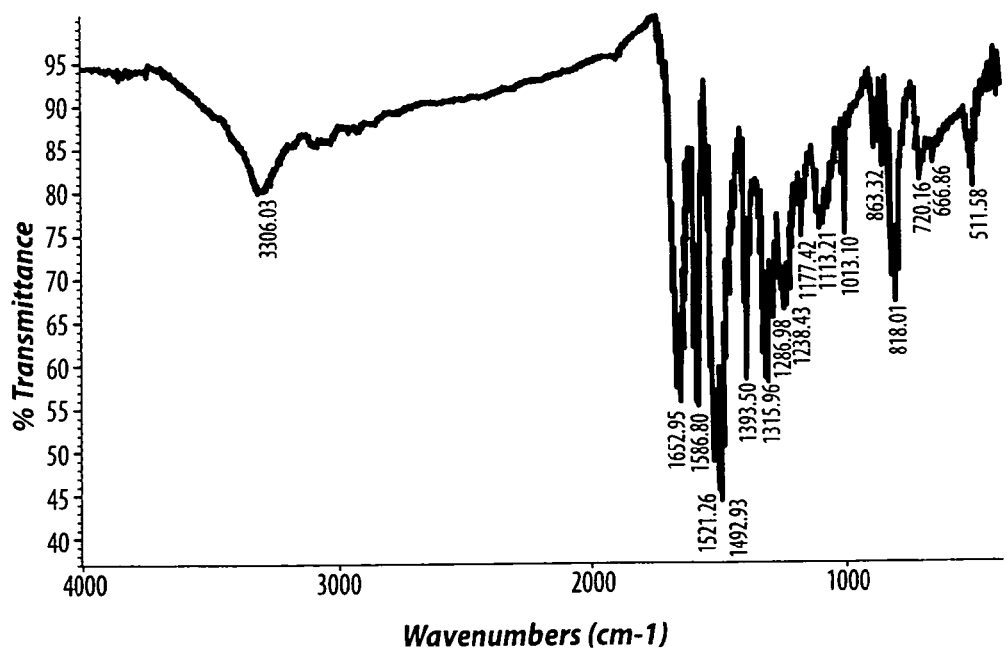

To 4-aminophenyl-disulfide (0.75 g, 3.0 mmole) was added NMP (17.5 mL) and pyridine (50 uL). This solution was stirred until fully dissolved. To this was then added terephthalic dichloride (0.61 g, 3.0 mmole). The resulting solution was stirred for 6 hours at room temperature under Ar. The reaction mixture was then poured into excess EtOH (100 mL) and a white solid immediately precipitated. The white solid was collected by filtration, washed with boiling EtOH (3×100 mL) and then dried under aspirator for 12 hours. The solid product was then collected and dried under vacuum for another 12 hours. 1.05 g of 2 was obtained as a solid white powder after drying. Product was characterized by $^1$H NMR in DMSO-d6 (FIG. 4a) and by infrared analysis (KBr pellet, FIG. 4b):

Thin Film Synthesis:

10 mg of the desired polymer was dissolved in 10 mL of DMSO. The solution was heated, vortexed, and sonicated until dissolved as much as possible. The liquid solution was then filtered to remove excess polymer that did not dissolve. This liquid was then pipetted onto glass slides (~100 uL) and then heated in an oven under nitrogen per the following program: RT to 189° C. over 2 hours followed by continued heating at 189° C. for 4 hours. The oven was then cooled to RT under $N_2$ and the glass slides removed. A thin, white film remained on the glass slides and the DMSO had been removed completely.

Polymer Degradation 2 mM solutions of 1 and 2 were prepared by dissolving ~1.8 mg of the polymer in 2.5 mL of NMP (freshly distilled). The 2 mM solutions of each polymer were irradiated with 266 nm light and analyzed by mass spectrometry (ESI MS), and the solutions showed no peaks over the mass range of 200-2000 amu. Each of the polymer solutions (1 mL) was then mixed with 1 mL of 15 wt % $H_2O_2$ and stirred for ~10 mins. The solutions were then analyzed by ESI MS and no peaks were observed in the range of 200-2000 amu.

Figure 5A:
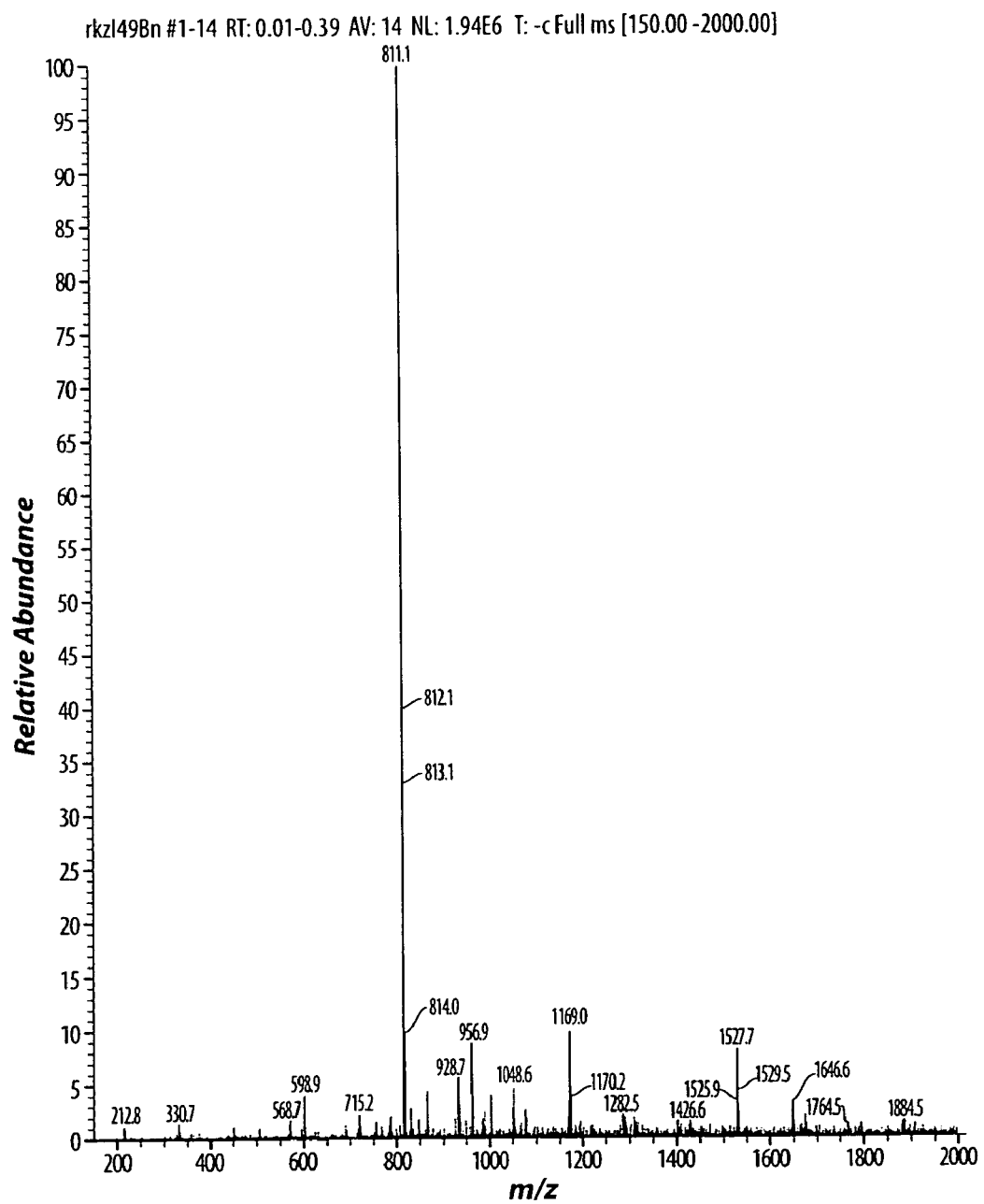
FIGS. 5a-5b depict mass spectral data for the degradation of polymers 1 and 2, respectively.
Figure 5B:
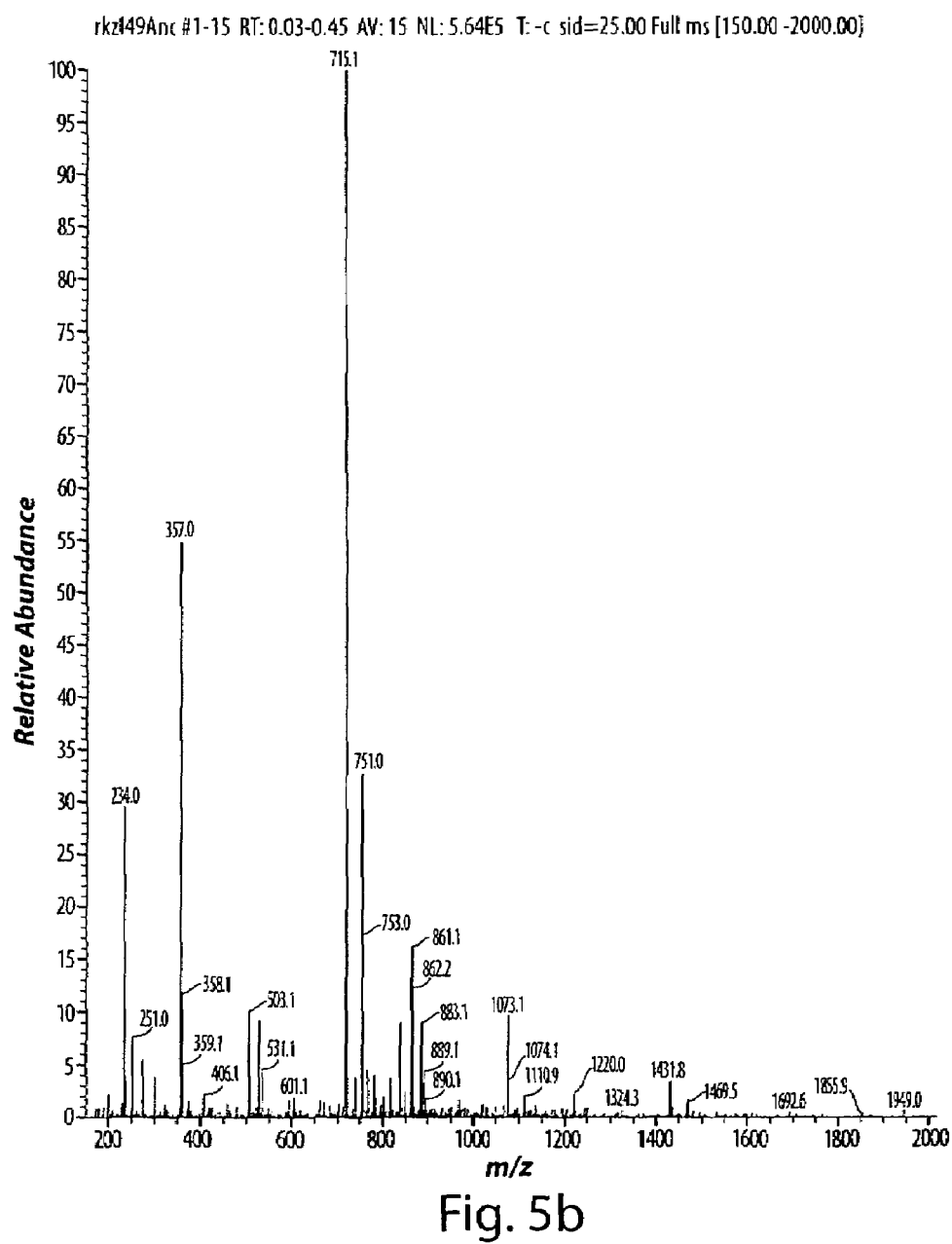

Freshly prepared polymer solutions were then prepared at 2 mM and 2.0 mL of each polymer solution was mixed with 1.0 mL of 15 wt % $H_2O_2$. These solutions were then irradiated at 266 nm for 2.0 minutes. The resulting solutions were then analyzed by ESI MS (FIG. 5a for 1, FIG. 5b for 2), and in the case of both polymers, low molecular weight fragments were now observed by ESI in the range of 200-2000 amu, indicating degradation in the presence of the two triggers.

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims.

The contents of all references, patents and published patent applications cited throughout this Application, as well as their associated figures are hereby incorporated by reference in entirety.

The invention claimed is:

1. A method for inducing degradation of a polymer in a patient, comprising:
   a) subjecting the polymer to an amount of a first trigger; and
   b) subjecting the polymer to an amount of a second trigger in the presence of the first trigger;
   thereby degrading the polymer in the patient,
   wherein the polymer substantially degrades in the presence of both the first and second trigger, and the polymer does not substantially degrade in the presence of either the first or second trigger alone, and
   wherein either the first trigger is hydrogen peroxide and the second trigger is light energy or the first trigger is light energy and the second trigger is hydrogen peroxide, the light energy being of a suitable wavelength to induce homolytic cleavage of one or more chemical bonds.

2. The method of claim 1, wherein the first trigger is hydrogen peroxide and the second trigger is the light energy.

3. The method of claim 2, wherein the polymer comprises sulfur-sulfur bonds in the backbone of the polymer and the light energy is of a suitable wavelength to induce homolytic cleavage of one or more of the sulfur-sulfur bonds.

4. The method of claim 3, wherein the light energy has a wavelength in the ultraviolet region.

5. The method of claim 4, wherein the light energy has a wavelength of between about 250 and 270 nm.

6. The method of claim 1, wherein the first trigger is the light energy and the second trigger is hydrogen peroxide.

7. The method of claim 1, wherein the polymer substantially degrades though the cleavage of carbon-oxygen bonds, carbon-nitrogen bonds, carbon-boron bonds, nitrogen-nitrogen bonds, sulfur-sulfur bonds, boron-oxygen bonds, oxygen-phosphorous bonds, or a combination thereof.

8. The method of claim 7, wherein the polymer substantially degrades though the cleavage of sulfur-sulfur bonds.
9. The method of claim 1, wherein the polymer is represented according to Formula III:
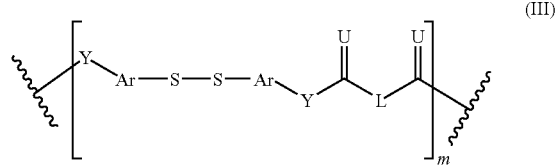
wherein,
Ar, independently for each occurrence, is an aryl or heteroaryl group;
U is O or S;
Y is NR", S, or O;
L is a linking group;
R" is H or lower alkyl; and
m is an integer greater than 10.
* * * * *